United States Patent [19]

De Simone

[11] Patent Number: 5,631,288
[45] Date of Patent: May 20, 1997

[54] THERAPEUTIC METHOD OF TREATING PATIENTS SUFFERING FROM AIDS AND AIDS-RELATED SYNDROMES AND ASYMPTOMATIC HIV-SEROPOSITIVE PATIENTS.

[75] Inventor: Claudio De Simone, Ardea, Italy

[73] Assignee: Sigma-Tau Industrie Farmaceutiche Riunite S.p.A., Rome, Italy

[21] Appl. No.: 370,357

[22] Filed: Jan. 9, 1995

Related U.S. Application Data

[63] Continuation of Ser. No. 115,050, Sep. 1, 1993, abandoned.

[30] Foreign Application Priority Data

Sep. 24, 1992 [IT] Italy ................... RM92A0693

[51] Int. Cl.$^6$ ................................................. A61K 31/35
[52] U.S. Cl. ................................................. 514/556
[58] Field of Search ................................. 514/556

[56] References Cited

U.S. PATENT DOCUMENTS 4,474,812  10/1984  Cavazza ................... 424/319
4,968,719  11/1990  Brevetti ................... 514/556

OTHER PUBLICATIONS

De Simone et al, *AIDS*, vol. 6, pp. 203–205 (1992).
Douvos et al 1991, PNAS vol. 88 pp 6328–6332.
Bogden et al 1990, Ann NY Acad Sci #587 pp. 189–195.
Scandurra et al. 1990 113CA109301b.
Marata et al. 1985 102CA218208v.

*Primary Examiner*—Russell Travers
*Attorney, Agent, or Firm*—Oblon, Spivak, McClelland, Maier & Neustadt, P.C.

[57] ABSTRACT

A novel therapeutical utilization of L-carnitine, acyl L-carnitines and the pharmacologically acceptable salts thereof is disclosed, for treating immune and metabolic alterations in patients suffering from AIDS and AIDS-related syndromes and in asymptomatic HIV-seropositive patients.

The L-carnitine amount to be administered according to this novel use is about 6–8 grams daily, via the oral route or an equivalent amount of an acyl L-carnitine or a pharmacologically acceptable salt thereof, i.e. three-four times as much the dose usually administered for the already known therapeutic uses of L-carnitine.

3 Claims, No Drawings

THERAPEUTIC METHOD OF TREATING PATIENTS SUFFERING FROM AIDS AND AIDS-RELATED SYNDROMES AND ASYMPTOMATIC HIV-SEROPOSITIVE PATIENTS.

This application is a continuation of application Ser. No. 08/115,050, filed on Sep. 1, 1993, now abandoned.

The present invention relates to a novel therapeutic use of L-carnitine, some alkanoyl L-carnitines and the pharmacologically acceptable salts thereof for treating the immune and metabolic alterations of patients suffering from AIDS and AIDS-related syndromes and asymptomatic HIV-seropositive patients.

By "AIDS-related syndromes", ARC (AIDS-related complex), LAS (lymphoadenopathy syndrome) and *Kaposi sarcoma* are meant.

More particularly, the present invention relates to a therapeutic method of restoring to normal altered immune and metabolic conditions in AIDS-patients and asymptomatic HIV-seropositive patients presenting normal or higher than normal serum levels of total carnitine, free carnitine and short-chain acyl carnitines by administering to them L-carnitine, an alkanoyl L-carnitine wherein the alkanoyl group, straight or branched, has 2–6 carbon atoms or a pharmacologically acceptable salt thereof.

Particularly preferred are acetyl, propionyl, butyryl, valeryl and isovaleryl L-carnitines.

Pharmaceutically acceptable salts of L-carnitine include all pharmaceutically acceptable salts which are prepared by the addition of an acid to L-carnitine, and which do not give rise to undesired toxic or side effects. The formation of pharmaceutically acceptable acid addition salts is well known in pharmaceutical technology.

Non limiting examples of suitable salts include the chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts.

For the sake of simplicity and clarity, hereinbelow reference will be made to L-carnitine only, it being understood, however, that whatever is disclosed in connection with L-carnitine equally applies to the above-identified acyl L-carnitines and pharmacologically acceptable salts thereof.

Previous therapeutical uses of L-carnitine are already known.

For instance, L-carnitine has been used in the cardiovascular field in the treatment of acute and chronic myocardial ischaemia, angina pectoris, cardiac arrhythmias and insufficiency. In nephrology, L-carnitine has been administered to chronic ureamic patients who are subject to regular heamodialysis treatment with a view to counteracting muscular asthenia and the onset of muscular cramps.

Further therapeutical uses are the restoration of HDL/ LDL+VLDL ratio to normal and in total parenteral nutrition.

The L-carnitine daily dose administered for the known therapeutical utilizations is about 10–30 mg/kg body weight or an equivalent amount of a pharmacologically acceptable salt thereof. Generally, a daily dose of 2 g L-carnitine is not exceeded.

However, there is no relationship between the foregoing known therapeutical utilizations of L-carnitine and the utilization which is the object of the present invention, either with regard to the etiology of the various pathologies treated or with regard to the administered L-carnitine dosages.

In AIDS subjects cardiac symptoms and muscle weakness have been attributed to drug toxicity, altered immunologic mechanisms and nutritional deficiency in addition to HIV infection (Stansell J. D.: Cardiac, endocrine and renal complications of HIV infection, in Medical Management of AIDS, editor Sande M. E., Volherding Pa. Philadelphia: W. B. Sanders Company, 1990, pp. 195–206).

Many of these patients are also hypometabolic as compared with healthy subjects.

In these patients wasting syndrome and cachexia are common manifestations (Stein et al.; Metabolism, 1990, 39: 876–881). Like symptoms—skeletal myopathy or cardiomyopathy or both—have been described in carnitine-depleted patients (Engel A. G., Angelini C.: Carnitine Deficiency of human skeletal muscle with associated lipid storage myopathy: a new syndrome, Science 1973, 173: 899–902; Waber L. J., Valle D., Neil C., Di Mauro S., Shug A: Carnitine deficiency presenting as familial cardiomyopathy: a treatable defect in carnitine transport:, J. Pediatr. 1982, 101: 700–705). As known, L-carnitine is necessary for the translocation of activated, long-chain fatty acids (AcylCoA) from cytoplasm across the inner mitochondrial membrane into the mitochodrion matrix where betaoxidation of fatty acids takes place.

Lack of L-carnitine impairs the transport of fatty acids into the mitochondria and consequently cell metabolism is shifted toward an activated glucose pathway, resulting into lipid accumulation and myocardial disturbances (Bremer J.: Carnitine, Metabolism and functions, Physiol. Rev. 1983, 63: 1420–1480).

That AIDS patients are carnitine-depleted has been confirmed by recent clinical studies (De Simone et al., AIDS, 1992, 6: 203–205).

Indeed, these studies have shown that remarkably lower than normal serum levels of total and free carnitine are presented by AIDS patients.

It has now been found that by administering L-carnitine, or one of the afore-said acyl L-carnitine or a pharmacologically acceptable salt thereof a whole set of immune and metabolic parameters (which will hereinbelow be more precisely defined) is remarkably improved in those AIDS patients who present normal or even higher than normal serum levels of total and free carnitine. This constitutes a surprising and unexpected result.

Furthermore, it has been found that this improvement can only be achieved by administering a daily dose of L-carnitine or an acyl L-carnitine which is 3–4 times as much the dose administered for all the therapeutical uses of the same active ingredients known to-date.

Preferably, about 6–8 g L-carnitine (or an equivalent amount of acyl L-carnitine or a pharmacologically acceptable salt thereof) are administered daily via the oral route.

CLINICAL TRIAL

The aim of this study was to evaluate the effects of L-carnitine supplementation on several immune and biochemical parameters of AIDS patients.

In order to obtain significant results in a small cohort of individuals and to eliminate the possible bias of effects due to the supplementation of L-carnitine to patients which were L-carnitine depleted, only AIDS patients with normal levels of total-carnitine (<47 µMol/L), and short-chain acyl-carnitines (<5 µMol/L) were enrolled (De Simone et al., AIDS 1992, 6: 203–205). In addition, only males were selected since the levels of carnitine in the blood vary according to sex (Denfel, J. Clin. Chem. Clin. Biochem. 1990, 28: 307–311).

Exclusion criteria were either abnormal serum creatine kinase levels or signs and symptoms pointing out muscle or cardiac dysfunction, such as enlargement or peaking of the T waves on electrocardiogram analysis and increased left ventricular wall thickness or hypertrophy on echocardiogram analysis, possibly reflecting either skeletal myopathy or cardiomyopathy or both which could occur in systemic carnitine deficiency.

Following the foregoing exclusion criteria, 28 patients were enrolled in this trial. All the patients were exintravenous drug addicts, aged from 26 to 48 years (mean age 36±2.4 yrs) and classified into the IVC1 group according CDC (Center for Disease Control) classification (MMWR 1987; 36; 1S), who gave their informed consent to be treated with either L-carnitine or placebo, in addition to the routine anti-infective therapy. All the patients had been administered Zidovudine (600 mg daily per os), intravenous immunoglobulins (400 mg/kg, every month) and trimethoprimsulphamethoxazole (15 mg/kg daily per os) for prophylaxis against *P. carinii* pneumonia, for 11±5 months (min. 4 months, max. 21 months). The patients were randomly assigned through computer generated numbers to receive either L-carnitine (6 g. per day for two weeks) or placebo. Fifteen, healthy controls who were age- and sex-matched to the AIDS patients were also enrolled.

Serum levels of total-carnitine, free-carnitine, and short-chain acyl-carnitines were measured by using the radioimmunoessay method of McGarry and Foster, Mc Garry J. D. et al., Methods of Enzymatic Analysis, Vol. VIII (Ed. Bergmejer J., Weinheim G. M.), Verlag Chemie GmbH, 1983, 474–81, with minor modifications (De Simone et al., AIDS 1991, 6: 203–205).

The statistical analysis was performed by using the Student's t test.

The results are shown in Table 1.

TABLE 1

EFFECT OF TREATMENT ON IMMUNE AND METABOLIC MARKERS IN AIDS PATIENTS.

| VARIABLE | L-CARNITINE | PLACEBO |
|---|---|---|
| TOTAL CARNITINE ($\mu$Mol/l) | | |
| pre-treatment | 55 ± 15 | 59 ± 9 |
| post-treatment | 84 ± 27 | 60 ± 6 |
| FREE CARNITINE | | |
| pre-treatment | 48 ± 13 | 51 ± 11 |
| post-treatment | 72 ± 26 | 49 ± 9 |
| SHORT CHAIN ACYL-CARNITINE ($\mu$Mol/l) | | |
| pre-treatment | 7 ± 2 | 8 ± 1 |
| post-treatment | 12 ± 3 | 7 ± 2 |
| CD4 COUNT (/$\mu$l) | | |
| pre-treatment | 70 ± 45 | 69 ± 39 |
| post treatment | 66 ± 43 | 63 ± 45 |
| LYMPHOCYTES $G_2$-M AND S PHASE CYCLE (%) | | |
| pre-treatment | 9.2 ± 3 | 8.7 ± 2 |
| post-treatment | 14 ± 3 | 9.1 ± 3 |
| LYMPHOCYTES $G_2$-M AND S PHASES CYCLE FOLLOWING SUPPLEMENTATION IN VITRO 100 $\mu$g/ml L-CARNITINE | | |
| pre-treatment | 12 ± 3 | 12.4 ± 4 |
| post-treatment | 13 ± 2 | 12.8 ± 2 |
| TNF-$\alpha$ (pg/mL) | | |
| pre-treatment | 21.3 ± 17 | 21.8 ± 10 |
| post-treatment | 13 ± 4 | 22 ± 9 |
| TRIGLYCERIDES (mg/dL) | | |
| pre-treatment | 528 ± 452 | 519 ± 418 |
| post treatment | 355 ± 332 | 523 ± 491 |
| $\beta$2-MICROGLOBULIN ($\mu$g/L) | | |
| pre-treatment | 2.470 ± 562 | 2.360 ± 512 |
| post treatment | 1.999 ± 749 | 2.382 ± 593 |

Although the daily dose to be administered depends, using sound professional judgement, upon body weight, age and general conditions exhibited by the patients, it has been found that it is generally suitable to administer to said patients from approximately 60 to approximately 120 mg/kg of body weight/day of L-carnitine or an equivalent amount of acyl L-carnitine or a pharmacologically acceptable salt thereof.

L-carnitine and the acyl L-carnitines are formulated with the usual excipients used for preparing orally or parenterally administrable compositions, well known to those expert in pharmaceutical technology.

Having regard to the high dose to be administered, a pharmaceutical composition in unit dosage form particularly suitable for the aforesaid therapeutical utilization comprises 1000 mg L-carnitine or an equivalent amount of an acyl L-carnitine or a pharmacologically acceptable salt thereof.

What is claimed is:

1. A method for normalizing the triglyceride and TNF-$\alpha$ levels in patients in need thereof, which patients suffer from AIDS and AIDS-related syndromes and in asymptomatic HIV-seropositive patients, which comprises administering to said patients about 6–8 g L-carnitine/day or an equivalent amount of a straight or unbranched chain $C_{2-6}$ alkanoyl L-carnitine or pharmaceutically acceptable salt thereof.

2. The method of claim 1 wherein the alkanoyl L-carnitine is selected from acetyl, propionyl, butyryl, valeryl and isovaleryl L-carnitine.

3. The method of claims 1 or 2 wherein the pharmacologically acceptable salt is selected from chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts.

* * * * *